United States Patent [19]

Hargrave et al.

[11] Patent Number: 5,571,809
[45] Date of Patent: Nov. 5, 1996

[54] THE TREATMENT OF HIV-1 INFECTION USING CERTAIN PYRIDODIAZEPINES

[75] Inventors: Karl D. Hargrave, Brookfield, Conn.; Gunther Schmidt, deceased, late of Munich, Germany, by Margaret Schmidt, legal representative; Wolfhard Engel, Biberach, Germany; Gunther Trummlitz, Warthausen, Germany; Wolfgang Eberlein, Biberach, Germany

[73] Assignee: Boehringer Ingelheim Pharmaceuticals, Inc., Ridgefield, Conn.

[21] Appl. No.: 291,634

[22] Filed: Aug. 17, 1994

Related U.S. Application Data

[63] Continuation of Ser. No. 154,844, Nov. 19, 1993, abandoned, which is a continuation of Ser. No. 26,353, Mar. 4, 1993, abandoned, which is a continuation of Ser. No. 897,734, Jun. 12, 1992, abandoned, which is a continuation of Ser. No. 768,453, Sep. 27, 1991, abandoned, which is a continuation of Ser. No. 600,547, Oct. 19, 1990, abandoned, which is a continuation of Ser. No. 584,409, Sep. 14, 1990, abandoned, which is a continuation of Ser. No. 438,570, Nov. 17, 1989, abandoned, which is a continuation of Ser. No. 372,732, Jun. 28, 1989, abandoned, which is a continuation of Ser. No. 340,973, Apr. 20, 1989, abandoned.

[51] Int. Cl.$^6$ .................... A61K 31/55; C07D 471/04; C07D 495/14
[52] U.S. Cl. ................ 514/220; 540/495; 540/557
[58] Field of Search .................. 540/495, 557; 514/220

[56] References Cited

U.S. PATENT DOCUMENTS 5,087,625  2/1992  Hargrave et al. .................... 514/220

Primary Examiner—Robert T. Bond
Attorney, Agent, or Firm—R. P. Raymond; A. Stempel; W. E. Rieder

[57] ABSTRACT

Disclosed are novel pyridodiazepines. These compounds, as well certain known 6,11-dihydro-5H-pyrido[2,3-b][1,5]benzodiazepin-5-ones are useful in the treatment of AIDS, ARC and related disorders associated with HIV infection.

12 Claims, No Drawings

THE TREATMENT OF HIV-1 INFECTION USING CERTAIN PYRIDODIAZEPINES

RELATED APPLICATIONS

This is a continuation of application Ser. No. 154,844, filed Nov. 19, 1993 now abandoned, which is a continuation of application Ser. No. 026,353, filed Mar. 4, 1993, now abandoned, which is a continuation of application Ser. No. 897,734, filed Jun. 12, 1992, now abandoned, which is a continuation of application Ser. No. 768,453, filed Sep. 27, 1991, now abandoned, which is a continuation of application Ser. No. 600,547, filed Oct. 19, 1990, now abandoned, which is a continuation of application Ser. No. 584,409, filed Sep. 14, 1990, now abandoned, which is a continuation of application Ser. No. 438,570, filed Nov. 17, 1989, now abandoned, which is a continuation of application Ser. No. 372,732, filed Jun. 28, 1989, now abandoned, which is a continuation of application Ser. No. 340,973, filed Apr. 20, 1989, now abandoned.

FIELD OF THE INVENTION

The invention relates to novel pyridodiazepines, methods for preparing these compounds, the use of these and related but known compounds in the treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must fast be converted into DNA, and then integrated into the host cell's genome, in order for the host cell to produce the required viral proteins.

The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA-dependent DNA polymerase. Acting fast as an RNA-dependent DNA polymerase, RT makes a single-stranded DNA copy of the viral RNA. Next, acting as a ribonuclease, RT frees the DNA just produced from the original viral RNA and then destroys the original RNA. Finally, acting as a DNA-dependent DNA polymerase, RT makes a second complementary, DNA strand, using the first DNA strand as a template. The two strands form double-stranded DNA, the form of DNA found in the host cell's genome, which is integrated into the host cell's genome by another enzyme, called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

SUMMARY OF THE INVENTION

A first aspect of the invention comprises novel pyridodiazepines. These possess inhibitory activity against HIV-1 RT. A second aspect of the invention comprises methods for making these novel compounds. A third aspect of the invention is a method for treating HIV-1 infection which comprises administering, to a human being exposed to or infected by HIV-1, a therapeutically effective amount of one of the above-mentioned novel compounds. A fourth aspect of the invention is a method for treating HIV-1 infection which comprises administering certain known 6,11-dihydro-5H-pyrido[2,3-b][1,5]-benzodiazepin-5-ones. These compounds also possess inhibitory activity against HIV-1 RT. Fifth and sixth aspects of the invention comprise novel 5-thione analogues of the above-mentioned known 5-ones, and a method for their preparation. A seventh aspect of the invention comprises a method for treating HIV-1 infection which comprises administering one or more of these novel 5-thione analogues. A final aspect of the invention comprises pharmaceutical compositions suitable for the treatment of HIV-1 infection comprising the above-mentioned compounds, both novel and known.

DETAILED DESCRIPTION OF THE INVENTION

In one of its composition of matter aspects, the invention comprises pyridodiazepines of the formula I

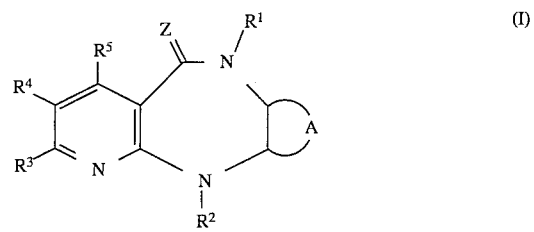

wherein,

A is a fused ring of the formula

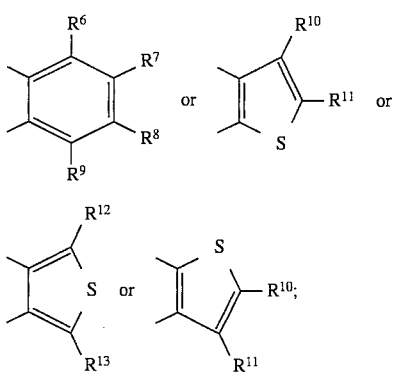

Z is oxygen, sulfur, =NCN, or a group of the formula =NOR$^{14}$ wherein R$^{14}$ is alkyl of 1 to 3 carbon atoms;

R$^1$ is hydrogen, alkyl or fluoroalkyl of 1 to 5 carbon atoms, cyclopropyl, alkenyl or alkynyl of 3 to 5 carbon atoms, 2-halo-propen-1-yl, arylmethyl (wherein the aryl moiety is phenyl, thienyl or furanyl, which is either unsubstituted or substituted by methyl, methoxy or halogen), alkanoyl of 2 to 3 carbon atoms, cyanoalkyl wherein the alkyl moiety contains 1 to 3 carbon atoms, or alkoxyalkyl or alkylthioalkyl of 2 to 4 carbon atoms;

$R^2$ is alkyl or fluoroalkyl of 1 to 5 carbon atoms, cycloalkyl of 3 to 5 carbon atoms, alkenyl or alkynyl of 2 to 5 carbon atoms, alkoxyalkyl or alkylthioalkyl of 2 to 4 carbon atoms, alkanoyl of 2 to 4 carbon atoms, hydroxyalkyl of 2 to 5 carbon atoms, arylmethyl (wherein the aryl moiety is phenyl, thienyl or furanyl, which is either unsubstituted or substituted by alkyl or alkoxy of 1 to 3 carbon atoms, hydroxyl, or halogen), phenyl (which is either unsubstituted or substituted by alkyl or alkoxy of 1 to 3 carbon atoms, halogen or hydroxyl) or alkoxy-carbonylmethyl wherein the alkoxy moiety contains 1 to 5 carbon atoms;

$R^3$, $R^4$, and $R^5$ are each independently hydrogen, alkyl of 1 to 3 carbon atoms or chloro, with the proviso that at least one of these substituents is hydrogen; or, one of $R^3$, $R^4$ and $R^5$ is butyl, alkanoyl of 1 to 3 carbon atoms, hydroxyalkyl of 1 to 4 carbon atoms, alkoxycarbonyl of 2 to 3 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkythio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- or di-alkylaminocarbonyl wherein each alkyl moiety contains 1 to 2 carbon atoms, carboxyalkyl of 2 to 3 carbon atoms, cyano, nitro, carboxyl, carbamyl, amino, azido or mono- or di-alkylaminoalkyl wherein the alkyl moieties each contain 1 to 2 carbon atoms, and the remaining two substituents are hydrogen or methyl; or, when Z is oxygen, one of $R^3$, $R^4$ and $R^5$ is alkylsulfinyl or alkylsulfonyl of 1 to 3 carbon atoms, with the proviso that the remaining two substituents are hydrogrogen or methyl;

$R^6$, $R^7$, $R^8$ and $R^9$ are each hydrogen; or, one of $R^6$, $R^7$, $R^8$ and $R^9$ is alkyl of 1 to 4 carbon atoms, alkanoyl of 1 to 3 carbon atoms, alkoxycarbonyl of 2 to 3 carbon atoms, hydroxyalkyl of 1 to 4 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- or di-alkylaminocarbonyl wherein each alkyl moiety contains 1 to 2 carbon atoms, carboxylalkyl of 2 to 3 carbon atoms, cyano, nitro, carboxyl, carbamyl, amino, azido or mono- or di-alkylaminoalkyl wherein each alkyl moiety contains 1 to 2 carbon atoms, and the remaining three substituents are hydrogen or two of the remaining three substituents are hydrogen and one is methyl, ethyl or halogen;

$R^{10}$ or $R^{11}$ is hydrogen, alkyl of 1 to 4 carbon atoms, cyano, nitro, halogen or alkanoyl of 1 to 3 carbon atoms, with the remaining substituent being hydrogen, chloro, methyl or ethyl; and, $R^{12}$ and $R^{13}$ are each independently hydrogen, alkyl of 1 to 4 carbon atoms, halogen or nitro.

A subgeneric aspect of the invention comprises compounds of the formula Ia

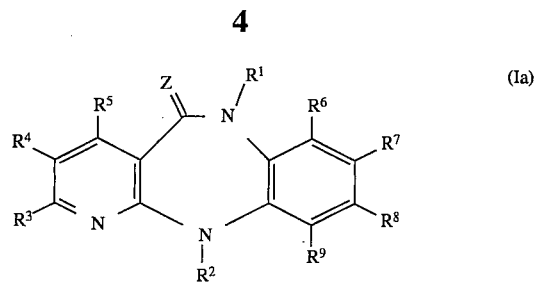

wherein,

Z is oxygen or sulfur;

$R^1$ is hydrogen, alkyl of 1 to 4 carbon atoms, alkenyl or alkynyl of 2 to 4 carbon atoms, 2-halo-propen-1-yl, or alkoxyalkyl or alkylthioalkyl of 2 to 3 carbon atoms;

$R^2$ is alkyl of 1 to 4 carbon atoms, cycloalkyl of 3 to 4 carbon atoms, alkenylmethyl or alkynylmethyl of 2 to 4 carbon atoms, alkoxyalkyl or alkylthioalkyl of 2 to 4 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy, hydroxyl or halogen), phenyl (which is either unsubstituted or substituted by methyl, methoxy, hydroxyl or halogen) or alkoxycarbonylmethyl wherein the alkoxy moiety contains 1 to 5 carbon atoms;

$R^3$, $R^4$, and $R^5$ are each independently hydrogen or methyl, with the proviso that at least one of these substituents is hydrogen, or $R^5$ is ethyl, propyl or butyl with the other two substituents being hydrogen;

$R^6$ is hydrogen, methyl, ethyl, chloro or trifluoromethyl with the proviso that $R^7$ is hydrogen, methyl or chloro;

$R^7$ is hydrogen, alkyl of 1 to 3 carbon atoms, alkanoyl of 1 to 3 carbon atoms, alkoxycarbonyl of 1 to 3 carbon atoms, hydroxyalkyl of 1 to 3 carbon atoms, alkoxycarbonylalkyl wherein the alkoxy and alkyl moieties each contain 1 to 2 carbon atoms, halogen, trifluoromethyl, hydroxyl, alkoxy or alkylthio of 1 to 2 carbon atoms, acetyloxy, alkanoylamino or aminoalkyl of 1 to 2 carbon atoms, cyano, nitro, amino, or mono- or di-methyl or -ethylamino, with the proviso that $R^8$ is hydrogen, methyl or chloro;

$R^8$ is hydrogen, alkyl of 1 to 3 carbon atoms, alkanoyl of 1 to 3 carbon atoms, alkoxycarbonyl of 1 to 3 carbon atoms, hydroxyalkyl of 1 to 3 carbon atoms, alkoxycarbonylalkyl wherein the alkoxy and alkyl moieties each contain 1 to 3 carbon atoms, halogen, trifluoromethyl, hydroxyl, alkoxy or alkylthio of 1 to 2 carbon atoms, acetyloxy, alkanoylamino or aminoalkyl of 1 to 2 carbon atoms, cyano, nitro, amino, or mono- or di-methyl or -ethylamino with the proviso that $R^7$ is hydrogen, methyl or chloro; or, when Z is oxygen and $R^8$ is hydrogen or methyl, $R^7$ may additionally be alkylsulfinyl or alkylsulfonyl of 1 to 2 carbon atoms, and when Z is oxygen and $R^7$ is hydrogen or methyl, $R^8$ may additionally be alkylsulfinyl or alkylsulfonyl of 1 to 2 carbon atoms; and, $R^9$ is hydrogen, methyl, ethyl, chloro or trifluoromethyl with the proviso that $R^8$ is hydrogen, methyl or chloro.

A further subgeneric aspect of the invention comprises compounds of formula Ia, wherein, Z is oxygen or sulfur, $R^1$ is hydrogen, alkyl of 1 to 3 carbon atoms, 2-halo-2-propen-1-yl, or alkoxyalkyl or alkylthioalkyl of two to three carbon atoms;

$R^2$ is alkyl of 1 to 4 carbon atoms, cycloalkyl of 3 to 4 carbon atoms, alkenyl or alkynyl of 2 to 4 carbon atoms, alkyloxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy or halogen) or alkoxycarbonylmethyl wherein the alkoxy moiety contains 1 to 5 carbon atoms; and, $R^3$ through $R^9$ are as set forth below in Table A.

TABLE A

| | $R^3$ | $R^4$ | $R^5$ | $R^6$ | $R^7$ | $R^8$ | $R^9$ |
|---|---|---|---|---|---|---|---|
| a | H | H | H | H | H | $CF_3$ | H |
| b | H | H | H | H | Cl | H | H |
| c | H | H | H | H | $CH_3$ | $CH_3$ | H |
| d | $CH_3$ | H | H | H | $CH_3$ | $CH_3$ | H |
| e | $CH_3$ | $CH_3$ | H | H | $CH_3$ | $CH_3$ | H |
| f | H | H | H | $CH_3$ | $CH_3$ | H | H |
| g | H | H | H | H | H | Cl | H |
| h | H | H | H | H | H | H | H |
| i | H | H | H | $CH_3$ | H | H | H |
| j | H | H | H | H | $CH_3O_2C$— | H | H |
| k | H | H | H | H | $C_2H_5O_2C$— | H | H |
| l | H | H | H | H | NC— | H | H |
| m | H | H | H | H | $CH_3CO$— | H | H |
| n | H | H | H | H | H | $CH_3O_2C$— | H |
| o | H | H | H | H | H | $C_2H_5O_2C$— | H |
| p | H | H | H | H | H | NC— | H |
| q | H | H | H | H | H | $CH_3CO$— | H |
| r | H | H | H | H | Cl | Cl | H |
| s | H | H | H | $CH_3$ | H | $CH_3$ | H |

A more particular subgeneric aspect of the invention comprises compounds of formula Ia wherein, Z is oxygen or sulfur;

$R^1$ is hydrogen, alkyl of 1 to 2 carbon atoms or allyl;

$R^2$ is alkyl of 2 to 3 carbon atoms, cyclopropyl or allyl; and $R^3$ through $R^9$ are each hydrogen, or $R^7$ and $R^8$ are both methyl or chloro and $R^3$, $R^4$, $R^5$, $R^6$ and $R^9$ are each hydrogen.

Compounds of Formula I may, if desired, be converted into their non-toxic, pharmaceutically acceptable acid addition salts by conventional methods; for example, by dissolving a compound of formula I in a suitable solvent and acidifying the solution with one of more molar equivalents of the desired acid. The invention also comprises such salts. Salt formation at any of $R^3$ through $R^9$, when any of these are basic amine functions, is preferred.

Examples of inorganic and organic acids which may form nontoxic, pharmaceutically acceptable acid addition salts with a compound of formula I are the following: hydrochloric acid, hydrobromic acid, sulfuric acid, phosphoric acid, nitric acid, tartaric acid, citric acid, methanesulfonic acid and the like. Compounds of the formual I usually form acid addition salts with one molar equivalent of the acid.

The compounds of Formula I can be prepared by known methods or obvious modifications thereof. Methods A through H, described below, are illustrative of the methods for preparing the compounds.

Method A

In Method A, a compound of Formula Ia, wherein Z is oxygen and both $R^1$ and $R^2$ and other than hydrogen, is prepared by converting a 6,11-dihydro-5H-pyrido[2,3-b][1,5]benzodiazepin-5-one of the formula II

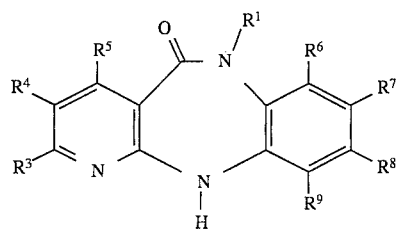

wherein $R^1$, $R^3$ through $R^9$ have the same meanings set forth with respect to Formula I but $R^1$ is other than H, into the corresponding 11-alkali metal compound, and the alkali metal compound is subsequently reacted with a compound of the formula $$R^2X \qquad (III)$$

wherein $R^2$ has the same meanings set forth with respect to formula I but in other than hydrogen, and X is a suitable leaving group such as chlorine, bromine or iodine, an appropriate radical of sulfuric acid, an aliphatic or aromatic sulfonic acid ester, or acyloxy.

The reaction is conveniently carried out as a one-batch process, wherein the alkali-metal salts obtained from a compound of formula II are not isolated from the reaction mixture but produced in situ, and, once formed, are reacted further in the same reaction medium.

The conversion of a compound of general formula II into the corresponding alkali metal compound may be effected by reacting a compound of formula II with a lithium alkyl (e.g. n-butyl lithium, or t-butyl lithium), optionally in the presence of tetramethylethylenediamine, a lithium dialkylamide, (e.g. lithium diisopropylamide, lithium dicyclohexylamide and lithium isopropylcyclohexylamide), a lithium aryl (e.g. phenyl lithium), alkali metal hydroxides (e.g. lithium, sodium or potassium hydroxide), alkali metal hydrides (e.g. sodium or potassium hydride) or alkali metal amides (e.g. sodium or potassium amides), or Grignard reagents (e.g. methyl magnesium iodide, ethyl magnesium bromide or phenyl magnesium bromide). The metallation is conveniently carried out in an inert organic solvent at temperatures of between −100° C. and the boiling point of the reaction mixture in question. If lithium alkyls, lithium aryls, lithium dialkylamides or Grignard reagents are used for the metallation, the preferred solvents are ethers such as tetrahydrofuran, diethyl ether or dioxan, optionally in a mixture with aliphatic or aromatic hydrocarbons, such as hexane or benzene, and the operation is carried out at temperatures of between −20° and +80° C. When metallation is effected with alkali metal hydrides and alkali metal amides, in addition to the solvents mentioned hereinbefore it is also possible to use xylene, toluene, acetonitrile, dimethylformamide and dimethylsulfoxide, while if alkali metal hydroxides are used it is also possible to use alcohols such as ethanol, methanol and aliphatic ketones such as acetone, as well as mixtures of these solvents with water.

For conversion of the alkali metal substituted 6,11-dihydro-5H-pyrido-[2,3-b][1,5]-benzodiazepin-5-one thus obtained into a compound of formula Ia, the solution or suspension of the alkali metal compound is reacted directly, i.e. without isolation of the reaction product with a compound of formula III at room or elevated temperatures, preferably at the boiling point of the solvent or suspension medium or at the boiling point of the compound III, whichever is lower.

It will be obvious to those skilled in the an that the presence of nucleophilic substituents in the compounds of formula II may require the use of an intermediate of formula II having substituents which are, other than the 11-position nitrogen, not nucleophilic but which can be derivatized to yield the required group. For example, amino or monoalkylamino substituents at any of $R^3$ through $R^9$ are preferably obtained by alkylating or acylating an intermediate of formula II having a nitro group at any of $R^3$ through $R^9$, and subsequently reducing the nitro group, and alkylating, if appropriate, to yield the final product.

The 6,11-dihydro-5H-pyrido[2,3-b][1,5]benzodiazepin-5-ones of formula II, which are used as starting materials, are either specifically described in U.S. Pat. Nos. 3,316,251 and 3,326,900, or can be prepared according to general procedures described therein.

Method B

In Method B, a compound of formula Ia, wherein Z is oxygen and $R^1$ is hydrogen, is obtained by hydrolyzing a compound of the formula IV

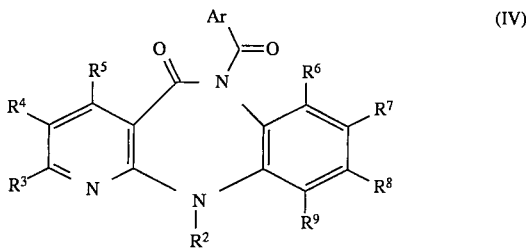

(IV)

wherein the groups $R^2$ through $R^9$ are as hereinbefore defined and Ar is an aromatic or heterocyclic group consisting of one or two nuclei which is or are optionally substituted by halogen, methyl or methoxy, e.g. phenyl, 4-bromophenyl, 1-naphthyl- or 4-pyridinyl.

The hydrolysis is carried out by the action of water or low molecular weight alcohols such as methanol, ethanol, 2-propanol, optionally in the presence of protic or aprotic co-solvents being miscible therein, such as tetrahydrofuran, 1,4-dioxane, dimethylformamide, dimethylacetamide, sulfolane, 1,3-dimethyl-2-imidazolidinone and, where appropriate, in the presence of alkaline or acid catalysts, at temperatures between 0° C. and the boiling point of the solvent mixture. As alkaline catalysts, alkali metal hydroxides such as lithium, sodium, calcium and barium hydroxide have proved to be suitable, and as acid catalysts, mineral acids, such as aqueous hydrochloric acid, hydrobromic acid, sulfuric acid or also methansulfonic acid or p-toluenesulfonic acid are preferred.

Starting materials of formula IV can be prepared by converting a 6-aroyl-6,11-dihydro-5H-pyrido[2,3-b][1,5]benzodiazepin-5-one of the formula V

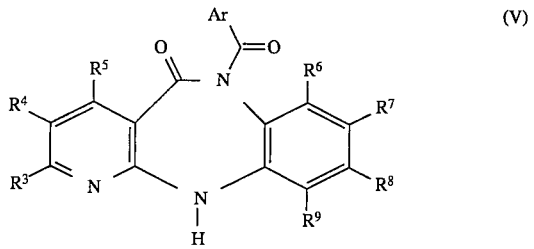

(V)

wherein Ar and $R^3$ through $R^9$ have the same meanings set forth with respect to formula IV, into the corresponding 11-alkali metal compound and reacting the alkali metal compound thus obtained with a compound of formula III.

The conversion of the compound of formula V into the corresponding alkali metal compound may be effected by reacting a compound of formula V with an alkali metal hydride, preferably lithium hydride, sodium hydride or potassium hydride. The reaction is preferably carried out at elevated temperatures and in the presence of an inert organic solvent such as absolute tetrahydrofuran or dimethylformamide.

For conversion of the alkali metal substituted 6-aroyl-6,11-dihydro-5H-pyrido[2,3-b][1,5]benzodiazepin-5-one thus obtained into a compound of formula IV, the solution or suspension of the alkali metal compound is reacted directly, i.e., without isolation, with a compound of formula III at room or elevated temperatures, preferably at the boiling point of the solvent or that of the compound of formula III.

Starting materials of formula V may be obtained by converting a compound of formula II wherein $R^1$ and $R^2$ are hydrogen atoms to its monosodium compound, preferably by reaction with 1 equivalent of sodium hydride in dimethylformamide, and reacting the alkali metal compound thus formed with an aroyl halide of the formula VI ArCOHal (VI)

wherein Ar has the same meanings as in compounds of formula IV, and Hal is chlorine, bromine or iodine.

It will be obvious to those skilled in the art that this method is not prefered in those cases wherein any of $R^2$ through $R^9$ are readily hydrolyzable substituents, for example, wherein $R^2$ is alkanoyl or any of $R^3$ through $R^9$ are alkanoylamino or alkoxycarbonyl. In cases wherein $R^2$ is alkanoyl or any of $R^3$ through $R^9$ are alkoxycarbonyl, for example, it is preferable to utilize method A described above. When $R^1$ is hydrogen two equivalents of base must be used. In cases wherein any of $R^3$ through $R^9$ are alkanoylamino, for example, it is preferable to carry out the hydrolysis (and subsequent acylation) on the corresponding nitro derivative, and then reduce the nitro moiety to the amine, followed by acylation to yield the desired product.

Method C

In Method C, a compound of the formula VII

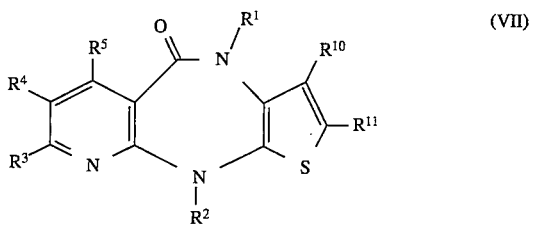

(VII)

wherein $R^1$ through $R^5$, $R^{10}$, and $R^{11}$ are as defined above, can be prepared from a compound of the formula VIII

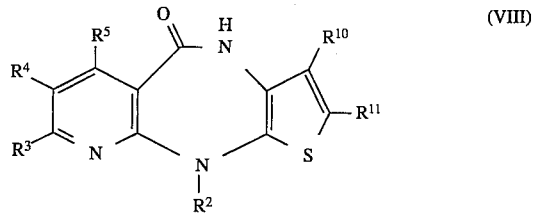

(VIII)

wherein $R^2$ through $R^5$, $R^{10}$ and $R^{11}$ are as defined above, by methods analogous to those described in Methods A and B. A compound of the formula VIII can be prepared by cyclization of a compound of the formula IXa or IXb, as described below, by known per se methods.

(IX)

[Structure IX]

IXa: $R^{16}$=NHR$^2$, $R^{17}$=hal

IXb: $R^{16}$=Cl, $R^{17}$=NHR$^2$

IXc: $R^{16}$=Cl, $R^{17}$=hal

IXd: $R^{16}$=Cl, $R^{17}$=H

IXe: $R^{16}$=Cl, $R^{17}$=NO$_2$

An amine of formula IXa can be prepared by known per se methods by reacting a chloro compound of, the formula IXc with an amine of the formula X $$R^2NH_2 \quad (X)$$

wherein $R^2$ is as defined above. A compound of the formula IXb can be prepared by known per se procedures, by nitration of a compound of the formula IXd, and then reduction and N-alkylation, by known procedures, of the resulting nitro compound of the formula IXe. An amide of the formula IXc can be prepared by known per se methods, by condensation of a chloronicotinic acid chloride of the formula XI with an amine of the formula XIIa.

(XI)

[Structure XI]

(XII)

[Structure XII]

XIIa: $R^{18}$=halogen

XIIb: $R^{18}$=H

An amide of the formula IXd can be prepared by known procedures, by condensation of a chloronicotinic acid chloride of the formula XI with an amine of the formula XIIb.

Starting materials are known from the literature, may be purchased or may be obtained by procedures known from the literature.

Method D

Using Method D, a compound of the formula XIII (XIII)

[Structure XIII]

wherein $R^1$ through $R^5$, $R^{12}$ and $R^{13}$ are as defined above, can be prepared from a compound of the formula XIV (XIV)

[Structure XIV]

wherein $R^2$ through $R^5$, $R^{12}$ and $R^{13}$ are as deemed above, by methods analogous to those described in Methods A and B. A compound of the formula XIV can be prepared by cyclization of a compound of the formula XV, by known per se methods.

(XV)

[Structure XV]

An amide of the formula XV, can be prepared by known per se methods, by condensation of a chloronicotinic acid chloride of the formula XI with an amine of the formula XVI.

(XVI)

[Structure XVI]

Starting materials are known from the literature, may be purchased or may be obtained by procedures known from the literature.

Method E

Using Method E, a compound of the formula XVII (XVII)

[Structure XVII]

wherein $R^1$ through $R^5$, $R^{10}$ and $R^{11}$ are as defined above, can be prepared from a compound of the formula XVIII (XVIII)

[Structure XVIII]

wherein $R^2$ through $R^5$, $R^{10}$ and $R^{11}$ are as defined above, by methods analogous to those described in Methods A and B. A compound of the formula XVIII can be prepared by cyclization of a compound of the formula XIXa by known per se methods.

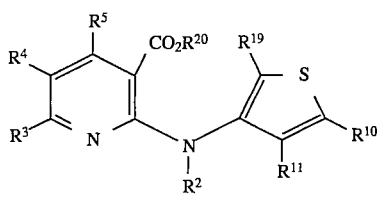

XIXa: $R^{19}=NH_2$, $R^{20}=C_{1-4}$ alkyl

XIXb: $R^{19}=NO_2$, $R^{20}=C_{1-4}$ alkyl

An amine of the formula XIXa can be prepared from the corresponding nitro compound of the formula XIXb by standard reduction procedures. A compound of formula XIX, wherein $R^{20}$ is alkyl of 1 to 4 carbon atoms can be prepared, by standard procedures, by estrification of a carboxylic acid of the formula XIX, wherein $R^{20}$ is hydrogen. A bis-arylamine of the formula XIXb can be prepared by condensation of an aminonicotinic acid of the formula XX

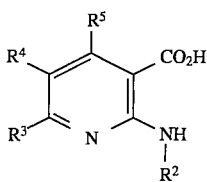

with a compound of the formula XXI using known per se methods.

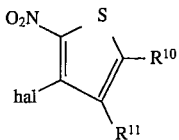

It will be obvious to those skilled in the art that compounds of the formula VIII, used as intermediates in Method C, can be prepared by a modification of Method E, wherein a thiophene of the formula XXII

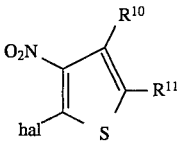

is condensed with an amine of the formula XX by known per se procedures.

Starting materials are known from the literature, may be purchased or may be obtained by procedures known from the literature.

Method F

In Method F, a compound of the formula I, wherein Z is sulfur, is obtained by reacting a compound of the formula I, wherein Z is oxygen, with a sulfurating agent, such as 2,4-bis(4-methoxyphenyl)-1,3-dithia-2,4-diphosphetane-2,4-disulfide; bis(tricyclohexyltin)sulfide; bis(tri-n-butyltin)sulfide; bis(triphenyltin)sulfide; bis(trimethylsilyl)sulfide or phosphorous pentasulfide. The reaction is carried out in an inert organic solvent such as carbon disulfide, benzene or toluene, at room temperature or higher, preferably an elevated temperature up to the boiling point of the reaction mixture, and preferably under anhydrous conditions. When using the above mentioned tin or silyl sulfide, it is preferable to carry out the sulfurization reaction in the presence of a Lewis acid such as boron trichloride.

It will be obvious to those skilled in the art that the presence of another carbonyl moiety in a compound of formula I, for example, a compound wherein Z is oxygen and any of $R^3$ through $R^9$ is alkanoyl, will require that the ketone carbonyl be protected via known methods by a suitable protecting group prior to the sulfurization reaction; deprotection subsequent to the sulfurization reaction provides the desired compound. Similarly, in cases wherein $R^2$ is, for example, alkanoyl, it will be obvious that the sulfurization reaction should be performed prior to the acylation of the 11-position nitrogen. In those cases wherein the substituents at any of $R^3$ through $R^9$ can be derived from nitro, for example, alkanoylamino, the sulfurization reaction can be performed on the corresponding nitro derivative, followed by an appropriate (known) reduction and finally acylation to yield the desired product.

Method G

Compounds of the formula I, wherein $R^1$ is hydrogen, A, and $R^2$ through $R^5$ are as defined above and Z is a group of formula =NCN, can be obtained by reacting a compound of the formula XXIII

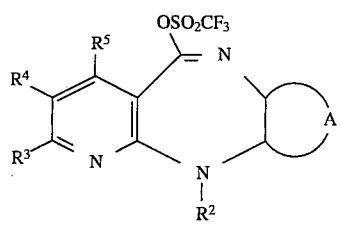

wherein A and $R^2$ through $R^5$ are as defined above, with cyanamide. The reaction is carried out in the presence of a base such as potassium carbonate, sodium carbonate, triethylamine, or diisopropylethylamine, and in an inert solvent such as methylene chloride, 1,4-dioxane, tetrahydrofuran, diethylether, chloroform, or dimethylformamide at a temperature between 0° C. up to the boiling point of the reaction mixture.

Method H

Compounds of the formula I, wherein $R^1$ is hydrogen and A and $R^2$ through $R^5$ are as defined above and Z is a group of formula =$NOR^{14}$, can be obtained, in a manner analogous to that of Method F, by reacting a compound of the formula XXIII, wherein $R^2$ through $R^5$ are as defined above with the appropriate alkoxylamine (O-alkylhydroxylamine) or its salt (for example, methoxylamine hydrochloride). The reaction is carried out under conditions analogous to those described for the treatment of compounds of the formula XI with cyanamide.

Starting Materials For Methods G and H

Compounds of the formula XXIII wherein A and $R^2$ through $R^5$ are as defined above, can be obtained by reacting a compound of the formula I, wherein $R^1$ is hydrogen and A and $R^2$ through $R^5$ are as defined above and Z is oxygen, with trifluoromethanesulfonic anhydride. The reaction is preferably carried out in an inert solvent using one to two equivalents of trifluoromethanesulfonic anhydride and in the presence of one to two equivalents of a base. The base may be, for example, a tertiary amine such as triethylamine or diisopropylethylamine, and the inert solvent used may include, for example, methylene chloride, chloroform, diethylether, tetrahydrofuran, or toluene. Addition of the reagents is generally carried out at or below ambient temperature, and the mixture is then allowed to react, at or near room temperature.

The alkoxylamine starting material may be purchase& are known from the literature or may be obtained by procedures known from the literature.

The above-described compounds of Formula I, and their salts, possess inhibitory activity against HIV-1 reverse transcriptase. When administered in suitable dosage forms, they are useful in the treatment of AIDS, ARC and related disorders associated with HIV infection. Another aspect of the invention, therefore, is a method for treating HIV-1 infection which comprises administering to a human being, exposed to or infected by HIV-1, a therapeutically effective amount of a novel compound of Formula I, as described above.

Yet another aspect of the invention comprises a method for treating HIV-1 infection which comprises administering, to a human being exposed to or infected by HIV-1, a therapeutically effective amount of one of the following known 6,11-dihydro-5H-pyrido[2,3-b][1,5]benzodiazepin-5-ones:

a) 2,4,6,8-tetramethyl-6,11-dihydro-5H-pyrido[2,3-b][1,5]-benzodiazepin-5-one;

b) 6-methyl-6,11-dihydro-5H-pyrido[2,3-b][1,5]benzodiazepin-5-one;

c) 6,11-dihydro-5H-pyrido[2,3-b][1,5]benzodiazepin-5-one;

d) 6-ethy-6,11-dihydro-5H-pyrido[2,3-b][1,5]benzodiazepin-5-one;

e) 6,8,9-trimethyl-6,11-dihydro-5H-pyrido[2,3-b][1,5]-benzodiazepin-5-one;

f) 6-ethyl-8,9-dimethyl-6,11-dihydro-5H-pyrido[2,3-b][1,5]-benzodiazepin-5-one;

g) 6-isobutyl-6,11-dihydro-5H-pyrido[2,3-b][1,5]benzodiazepin-5-one; and, h) 6-ethyl-9-methyl-6,11-dihydro-5H-pyrido[2,3-b][1,5]-benzodiazepin-5-one.

The above named known compounds also inhibit HIV-1 reverse transcriptase (HIV-1 RT).

A further aspect of the invention comprises the novel 5-thione analogues of the above-mentioned known compounds. These 5-thione analogues can be prepared from the known 5-ones using the sulfurization reaction described in Method F, above. These analogues also inhibit HIV-1 RT and the invention further comprises a method for treating HIV-1 infection which comprises administering, to a human being exposed to or infected by HIV-1, a therapeutically effective mount of one or more of these 5-thione analogues.

The above described compounds of formula I, the known compounds named above, and the 5-thione analogues of these known compounds may be administered in single or divided doses by the oral, parenteral or topical routes. A suitable oral dosage for such compounds would be in the range of about 10 to 500 mg per day. In parenteral formulations, a suitable dosage unit may contain from about 1 to 50 mg of said compounds, whereas for topical administration, formulations containing about 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When these compounds are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene glycols, petroleum jelly and the like. The pharmaceutical preparations can be prepared in a conventional manner and finished dosage forms can be solid dosage forms, for example, tablets, dragees, capsules, and the like, or liquid dosage forms, for example, solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, these compounds can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The above described compounds can also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chlorobutanol or phenylethyl alcohol.

Additionally, these compounds can be administered by suppository.

As stated before, the above described compounds inhibit the enzymatic activity of HIV-1 RT. Based upon testing of these compounds, as described below, it is known that they inhibit the RNA-dependent DNA polymerase activity of HIV-1 RT. Based upon other testing, not described herein, it is believed that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds of formula I described in the Examples which appear below were so tested. The results of this testing appear in Table I, below. The above-named known compounds were also so tested. The results of this testing appear in Table II, below.

REVERSE TRANSCRIPTASE (RT) ASSAY

Assay Theory:

Among the enzymes for which Human Immunodeficiency Virus (HIV-1) encodes is a reverse transcriptase (1); so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate.

Materials:

a) Preparation of the enzyme

Reverse transcriptase enzyme from the LAV strain of Human Immunodeficiency Virus (HIV-1) (1) was isolated from the bacterial strain JM109 (3) expressing the DNA clone pBRTprtl+ (2) which is under the control of the lac promotor in the expression vector plBI21 (4). An overnight culture grown in 2XYT medium (37° C., 225 rpm) (5) supplemented with 100 µg/ml ampicillin for positive selection is inoculated at a 1:40 dilution into M9 medium supplemented with 10 µg/ml thiamine, 0.5% casamino acids, and 50 µg/ml ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/ml) for 30 minutes on ice. The cells are lysed by the addition of 0.2% NP-40 and brought to 1M NACl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2× concentrated stock reaction mixture

| Stock Reagent | 2X Mix Concentration |
|---|---|
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 µg/ml |
| $^3$H-dGTP (81 µM) | 0.6 µM |

Assay Procedure:

The 2× concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 µl/well; 3 wells/compound). The HIV-1 RT enzyme is thawed, diluted in 50 mM Tris pH 7.4 so that fifteen µl of diluted enzyme contain 0.001 Unit (one unit is that mount of enzyme to transform 1 micromole of substrate per minute at 25° C.), and fifteen µl are dispensed per well. Twenty µl of 0.12–0.5M EDTA are added to the first three wells of the microtiter plate. EDTA chelates the $Mg^{++}$ present and prevents reverse transcription. This group serves as background polymerization which is subtracted from all other groups. Twenty-five ul of the 2× reaction mixture are added to all wells and the assay is allowed to incubate at room temperature for 60 minutes. The assay is terminated by precipitating the DNA in each well with 50 µl of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mls of scintillation cocktail and is counted in a Beckman beta counter.

The calculation for percent inhibition is as follows:

$$\% \text{ inhibition} = \frac{CPM \text{ Mean Test Value} - CPM \text{ Mean Control Value} \times 100}{CPM \text{ Mean Control Value}}$$

References:
1. Benn, S., et at., *Science* 230:949, 1985
2. Farmerie, W. G. et. al., *Science* 236:305, 1987
3. Yanisch-Perron, C., Viera, J., and Messing, J., *Gene* 33:103, 1985
4. International Biotechnologies, Inc., New Haven, Conn. 06535
5. Maniatis, T, Fritsch, E. F., and J. Sambrook, eds. *Molecular Cloning: A Laboratory Manual*, Cold Spring Harbor Laboratory, 1982
6. Spira, T., et. at. *J. Clinical Microbiology*, 25:97, 1987.

In order to confirm that compounds which are active in the RT Assay also have the ability to inhibit HIV replication in a living system, compounds of formula I were also tested in the human T-Cell Culture Assay described below. The results of this testing appear in Table I.

HUMAN T-CELL CULTURE ASSAY

Assay Theory: Formation of syncytia is a feature of in vitro cultures of CD4+T-cells infected with HIV-1. In this assay, T-cells are treated with a putative replication inhibiting compound and then infected with HIV-1. After incubation, the culture is checked for the formation of syncytia. The absence or reduction in the number of syncytia is used as a measure of the test compound's ability to inhibit HIV replication.

Assay Method: The target cells, designated c8166, are a subclone of human lymphoma cells of T-cell origin and are established at an initial density of $5 \times 10^4$ per 100 µl in RPMI 1640 (+10% fetal bovine serum) culture medium in 96 well flat bottom plates. A selected amount of test compound, dissolved in DMSO, is included. After 24 hours, 50–100 $TCID_{50}$'s (the dose that results in induced effect in 50% of test cultures) of the HTLV-IIIB strain of HIV-1 (2) are inoculated into each culture. Control cultures receive compound or virus only. Four days after virus challenge, cultures are visually examined for the frequency and distribution of virus-induced giant cell syncytia. The percent inhibition by the test compound is determined by comparison with control values. Confirmation of the presence or absence of virus replication is accomplished by harvesting the cell free culture fluids from all experimental groups to determine the presence or absence of infectious progeny through the induction of syncytia formation in secondary human T-cell cultures after 3 days.

References:
(1) M. Somasundaran and H. L. Robinson, *Science* 242, 1554 (1988).
(2) G. M. Shaw, R. H. Hahn, S. K. Arya, J. E. Groopman, R. C. Gallo and F. Wong-Staal, *Science* 226, 1165 (1984)

In order to assess the specificity of the enzyme inhibitory activity of the compounds of formula I, provided by the invention, and the known compounds, a few were tested, using known per se assay methods, for their ability to inhibit Feline Leukemia Virus-derived reverse transcriptase and Calf Thymus-derived DNA alpha-polymerase. None of the compounds so tested was observed to possess any inhibitory activity against these enzymes.

These results indicate that the enzyme inhibitory activity of the compounds provided by the invention is directed rather specifically against HIV-1 RT.

In order to roughly assess the cytotoxicity of the compounds of formula I, several such compounds were tested in the MTT Cellular Cytotoxicity Assay described below. The results of this testing are reported in Table I, below. Compounds having a relatively high $EC_{50}$ are preferred.

MTT ASSAY FOR CELLULAR CYTOTOXICITY

Assay Theory:

The MTT [3-(4,5-dimethylthiazol-2-yl)-2,5 diphenyl tetrazolium bromide) assay is based on cleavage of tetrazolium bromide by metabolically active cells, resulting in a highly quantitative blue color. This assay has been previously described (1) but has been optimized for the purposes of the testing reported herein.

Assay Method:

The H9 cell line (2), an established human lymphoma suspension cell line grown in RPMI 1640 supplemented with 10% fetal bovine serum, is used as the target cell line in the assay. Cells (100 μl) are plated in microtest plate wells at a concentration of $10^5$ cells per ml in the presence of varying concentrations of inhibitor. The cells are incubated at 37° C. in a humidified $CO_2$ incubator. Five days later, 20 μl of MTT (5 mg/ml in RPMI 1640, sonicated, 0.2 micron filtered, and stored at 4° C.) is added to each well. After 4 hours additional incubation at 37° C., 60 μl of Triton-X is added to each well and thoroughly mixed to aid the solubilization of the crystals. Absolute ethanol (5 μl) is added to each well and the resulting mixture is incubated for 30 minutes at 60° C. and immediately read on a plate reader (Dynatech) at a wavelength of 570 nm.

Data from this assay are used to generate a nonlinear regression analysis which yields an $EC_{50}$.

References:
1. Mosmann, Tim, *J. Immunol.* Methods, 65:55, 1983.
2. Jacobs, J. P., *J. Natl. Cancer Inst.*, 34:231, 1965.

TABLE I

| Compound of Example No. | RT Inhibition % @ 10 μg/ml | T-Cell Culture Assay (% inhibition) | Cytotoxicity Assay ($EC_{50}$) |
|---|---|---|---|
| 1 | 37 | NT | NT |
| 2 | 97 | 100% @ 4 μM | 80 μM |
| 3 | 92 | NT | NT |
| 4 | 79 | " | 49 μM |
| 5 | 94 | 100% @ 19 μM | 50 μM |
| 6 | 46 | NT | NT |
| 7 | 50 | " | " |
| 8 | 55 | " | 37 μM |
| 9 | 92 | " | 4 μM |
| 10 | 68 | " | NT |
| 11 | 88 | " | " |
| 12 | 89 | " | " |
| 13 | 91 | " | " |
| 14 | 75 | " | " |
| 15 | 39 | " | 18 |
| 16 | 44 | " | NT |
| 17 | 49 | " | 9 |
| 18 | 29 | " | NT |
| 19 | 90 | " | 85 |
| 20 | 69 | " | NT |
| 21 | 96 | " | " |
| 22 | 100 | 100% @ 3 μM | " |
| 23 | 100 | NT | " |
| 24 | 100 | " | " |

TABLE I-continued

| Compound of Example No. | RT Inhibition % @ 10 μg/ml | T-Cell Culture Assay (% inhibition) | Cytotoxicity Assay ($EC_{50}$) |
|---|---|---|---|
| 25 | 73 | " | " |
| 26 | 81 | " | " |
| 27 | 64 | " | " |
| 28 | 65 | " | " |
| 29 | 99 | " | " |
| 30 | 94 | " | " |
| 31 | 92 | " | " |
| 32 | 51 | " | " |
| 33 | 97 | " | " |
| 34 | 85 | " | " |
| 35 | 99 | " | " |
| 36 | 89 | " | " |

Note: NT = not tested

TABLE II

| Known Compound | RT Inhibition % @ 10 μg/ml |
|---|---|
| a | 58 |
| b | 43 |
| c | 22 |
| d | 69 |
| e | 65 |
| f | 95 |
| g | 33 |
| h | 78 |

The following examples further illustrate the present invention and will enable others skilled in the art to understand the invention more completely. It should be understood, however, that the invention is not limited to the particulars given in the examples.

EXAMPLE 1

6,11-Dihydro-11-methyl-5H-pyrido[2,3-b][1,5]-benzodiazepin-5-one a) 6-Benzoyl-6,11-dihydro-5H-pyrido[2,3-b ][1,5]benzodiazepin-5-one A suspension of 14.8 g (0.07 mol) of 6,11-dihydro-5H-pyrido[2,3-b]1,5]benzodiazepin-5-one in 200 ml dimethylformamide was heated to 120° C., cooled down to 80° C. after complete dissolution, whereupon 2.2 g (0.074 mol) of an 80% dispersion of sodium hydride in mineral oil were added. Thereafter, the mixture was stirred at 60° C. for 45 minutes, 8.6 ml (0.075 mol) of benzoyl chloride were dropped in and the reaction mixture was stirred at the same temperature for a further 15 minutes. The mixture was cooled to room temperature and after being stirred for two hours was set aside overnight. The resulting precipitate, mostly consisting of starting material, was filtered off. The filtrate was then evaporated in vacuo, the residue was admixed with 100 ml of water and 100 ml of dichloromethane and filtered again. The organic phase was separated and evaporated in vacuo. The oily residue was recrystallized from chloroform/ethylacetate 1/1 (v/v) yielding slightly yellowish crystals of m.p. 198°–201° C. which were identified as 6-benzoyl-6,11 -dihydro-5H-pyrido[2,3-b][1,5]benzodiazepin-5-one. The yield was 3.5 g (16% of theory).

b) 6-Benzoyl-6,11-dihydro-11-methyl-5H-pyrido[2,3-b][1,5]-benzodiazepin-5-one 12.67 g (0.06 mol) of the product obtained in step a) were dissolved in 190 ml of absolute dimethylformamide and the resulting solution was admixed with 1.95 g (0.065 mol) of an 80% dispersion of sodium hydride in mineral oil, whereupon hydrogen evolved and the mixture became reddish and slightly warm. The mixture was stirred at room temperature for 15 minutes, then cooled to +10° C. and admixed with 4.38 ml (0.07 mol) of methyl iodide and subsequently was stirred at room temperature for a further 45 minutes. The solvent was removed by distillation in vacuo. The residue was washed with water, dissolved in hot ethanol and the resulting solution was treated with charcoal and filtered while hot. The filtrate was set aside at room temperature for several hours, and the resulting precipitate was filtered by suction. The product had a m.p. of 181°–183° C. and was identified as 6-benzoyl-6,11-dihydro-11-methyl-5H-pyrido-[2,3-b][1,5]benzodiazepin-5-one. The yield was 12.54 g (63% of theory).

c) 6,11-Dihydro-11-methyl-5H-pyrido[2,3-b][1,5]benzodiazepin-5-one

A mixture of 9.4 g (0.0285 mol) of the product obtained in step b, 150 ml ethanol and 5 ml concentrated aqueous hydrochloric acid was refluxed for five hours while stirring. The clear yellowish solution that had been formed was set aside overnight. The resulting precipitate was collected by filtration and thoroughly washed with diluted aqueous ammonia. The product was dried overnight in a stream of nitrogen at room temperature and thereafter was recrystallized from n-propanol. The colorless product had a m.p. of 235°–237° C. and was identified as 6,11-dihydro-11-methyl-5H-pyrido-[2,3-b][1,5]benzodiazepin-5-one. The yield was 3.3 g (51% of theory).

EXAMPLE 2

6,11-Dihydro-11-ethyl-6-methyl-5H-pyrido[2,3-b][1,5]-benzodiazepin-5-one

Under nitrogen cover, 7.90 g (0.035 mol) of 6,11-dihydro-6-methyl-5H-pyrido[2,3 -b][1,5]benzodiazepin-5-one were suspended in 79 ml of anhydrous dimethylformamide. To this suspension 1.25 g (0.052 mol) of sodium hydride were added in small portions within 10 minutes. The temperature arose to 60° C. with development of hydrogen. Stirring was continued for a further 45 minutes at the same temperature. Afterwards, the batch was left to cool to ambient temperature. Ethyl iodide (3.38 ml; 6.534 g, 0.0419 mol) was dropped in within about 10 minutes. The batch was stirred for further 15 minutes at ambient temperature. After this time no starting material was found in the reaction mixture by thin-layer-chromatography.

In order to destroy-still present sodium hydride, 1 ml of methanol was added. The reaction mixture was evaporated in vacuo, and the residue was distributed between 100 ml of chloroform and 100 ml of water, the red organic phase was dried over sodium sulfate, 1 g of charcoal was stirred in, the batch was filtered and the filtrate was evaporated to dryness in vacuo. The high viscous red oil obtained was purified by column chromatography using 300 g of silica gel (0.2–0.5 mm) and as eluent chloroform/ethyl acetate 1/1 (v/v). By evaporation of the fraction containing the compound, 7.0 g of a slightly red colored product were obtained, which was recrystallized with cyclohexane, yielding 5 g (56% of theory) of 6,11 -dihydro-11-ethyl-6-methyl-5H-pyrido[2,3-b][1,5]benzodiazepin-5-one as colorless crystals of m.p. 106°–111° C.

EXAMPLE 3

6,11-Dihydro-6-methyl-11-propyl-5H-pyrido-[2,3-b][1,5]benzodiazepin-5-one

Using a procedure analogous to that described in Example 2, the product 6,11-dihydro-6 -methyl-11-propyl-5H-pyrido [2,3-b][1,5]benzodiazepin-5-one, m.p. 96°–98° C. (recrystal from petroleum ether) was prepared from 6,11-dihydro-6-methyl-5H-pyrido[2,3-b][1,5]benzodiazepin-5-one and 1-iodopropane. The yield was 36% of theory.

EXAMPLE 4

6,11-Dihydro-6,11-dimethyl-9-(trifluoromethyl)-5H-pyrido[2,3-b][1,5]benzodiazepin-5-one a) 6,11-Dihydro-6-methyl-9-(trifluoromethyl)-5H-pyrido[2,3-b][1,5]benzodiazepin-5-one 13.26 g (0.475 mol) of 6,11-dihydro-9-(trifluoromethyl)-5H-pyrido[2,3-b][1,5]benzodiazepin-5-one were dissolved in a mixture consisting of 40 ml of a potassium tert. butoxide solution (from 2.14 g of potassium and 40 ml of tert. butanol) and 100 ml of absolute dioxane, and the resulting solution was refluxed for two hours. Thereafter, 14.2 g (0.1 mol) of methyliodide were added and the mixture was refluxed for four hours. The reaction mixture was then filtered to remove the precipitated potassium iodide, and the filtrate was evaporated in vacuo. The residue was recrystallized from ethanol, yielding a compound having a melting point of 169°–172° C. which was identified to be 6,11-dihydro-6-methyl-9-(trifluoromethyl)-5 H-pyrido[2,3-b][1,5]benzodiazepin-5-one. The yield was 26% of theory.

b) 6,11-Dihydro-6,11-dimethyl-9-(trifluoromethyl)-5H-pyrido[2,3-b][1,5]benzodiazepin-5 -one Using a procedure analogous to that described in Example 2, the product 6,11-dihydro-6,11 -dimethyl-9-(trifluoromethyl)-5H-pyrido-[2,3-b][1,5]benzodiazepin-5-one, m.p. 142°–145° C. (recrystallized from ethanol) was prepared from the product of step a) and methyl iodide. The yield was 48% of theory.

EXAMPLE 5

6,11-Dihydro-6-methyl-11-isopropyl-5H-pyrido-[2,3-b][1,5]benzodiazepin-5-one

Using a procedure analogous to that described in Example 2, the product 6,11-Dihydro-6 -methyl-11-isopropyl-5H-pyrido[2,3-b][1,5]benzodiazepin-5-one, m.p. 144°–147° C. (recrystallized from cyclohexane) was prepared from 6,11-Dihydro-6-methyl-5H-pyrido[2,3-b][1,5]benzodiazepin-5-one and 2-bromopropane. The yield was 17% of theory.

EXAMPLE 6

11-Butyl-6,11-dihydro-6-methyl-5H-pyrido-[2,3-b][1,5]benzodiazepin-5-one

Using a procedure analogous to that described in Example 2, the product 11-butyl-6,11 -dihydro-6-methyl-5H-pyrido [2,3-b][1,5]benzodiazepin-5-one, m.p. 56°–58° C. (recrystallized from petroleum ether) was prepared from 6,11-dihydro-6-methyl-5H-pyrido[2,3-b][1,5]benzodiazepin-5-one, and 1-iodobutane. The yield was 40% of theory.

EXAMPLE 7

6,11-Dihydro-11-(2-hydroxyethyl)-6-methyl-5H-pyrido[2,3-b][1,5]benzodiazepin-5-one Using a procedure analogous to that described in Example 2, 22.52 g (0.1 mol) of 6,11 -dihydro-6-methyl-5H-pyrido [2,3-b][1,5]benzodiazepin-5-one were convened to 6,11-dihydro-6-methyl-11-[2-[(2-tetrahydropyranyl)oxy]ethyl]-5H-pyrido-[2,3-b][1,5]benzodiazepin- 5-one by reaction with 21.8 g (0.132 mol) of 1-chloro-2-[(2-tetrahydropyranyl)-oxy]-ethane. The raw material thus obtained was dissolved in a mixture of 500 ml ethanol and 100 ml of concentrated aqueous hydrochloric acid. After having been refluxed for two hours, the reaction mixture was evaporated in vacuo. The residue was triturated with ethanol, the precipitated crystals were faltered off and the solvent was removed from the filtrate by distillation in vacuo. The residue was purified by column chromatography on silica gel (0.2–0.5 mm) using chloroform/ethylacetate/methanol 5/5/1 (v/v/v) as an eluent. Colorless crystals of m.p. 133°–134° C. (after recrystallization from xylene) were obtained in a yield of 9.0 g (33% of theory).

EXAMPLE 8

8-Chloro-6,11-dihydro-6,11-dimethyl-5H-pyrido-[2,3-b][1,5]benzodiazepin-5-one

Using a procedure analogous to that described in Example 2, the product 8-chloro-6,11 -dihydro-6,11-dimethyl-5H-pyrido[2,3-b][1,5]benzodiazepin-5-one, m.p. 188°–189° C. (recrystallized from ethanol) was prepared from 8-chloro-6,11-dihydro-6-methyl-5H pyrido[2,3-b][1,5]benzodiazepin-5-one and methyl iodide. The yield was 33% theory.

EXAMPLE 9

6,11-Dihydro-6,8,9,11-tetramethyl-5H-pyrido-[2,3-b][1,5]benzodiazepin-5-one

Using a procedure analogous to that described in Example 2, the product 6,11-dihydro-6,8,9,11-tetramethyl-5H-pyrido[2,3-b][1,5]benzodiazepin-5-one, m.p. 189°–192° C. (recrystallized twice from ethanol) was prepared from 6,11-dihydro-6,8,9-trimethyl-5H-pyrido-2,3 -b][1,5]benzodiazepin-5-one and methyl iodide. The yield was 47% of theory.

EXAMPLE 10

6,11-Dihydro-6,11-dimethyl-5H-pyrido-[2,3-b][1,5]benzodiazepin-5-one

Using a procedure analogous to that described in Example 2, the product 6,11-Dihydro-6,11 -dimethyl-5H-pyrido[2,3-b][1,5]benzodiazepin-5-one, m.p. 126°–128° C. (recrystallized from cyclohexane) was prepared from 6,11-dihydro-6-methyl-5H-pyrido[2,3-b][1,5]benzodiazepin-5-one and methyl iodide. The yield was 53% of theory.

EXAMPLE 11

6,11-Dihydro-6-ethyl-11-methyl-5H-pyrido-[2,3-b][1,5]benzodiazepin-5-one

Using a procedure analogous to that described in Example 2, the product 6,11-dihydro-6-ethyl-11-methyl-5H-pyrido[2,3-b][1,5]benzodiazepin-5-one, m.p. 118°–119° C. (recrystallized twice from cyclohexane) was prepared from 6,11-dihydro-6-ethyl-5H-pyrido-[2,3-b][1,5]benzodiazepin-5-one and methyl iodide. The yield was 53% of theory.

EXAMPLE 12

6,11-Dihydro-11-methyl-6-propyl-5H-pyrido-[2,3-b][1,5]benzodiazepin-5-one

Using a procedure analogous to that described in Example 2, the product 6,11-dihydro-11 -methyl-6-propyl-5H-pyrido[2,3-b][1,5]benzodiazepin-5-one, m.p. 95.5°–97.5° C. (recrystallized from petroleum ether) was prepared from 6,11-dihydro-6-propyl-5H-pyrido[2,3-b][1,5]benzodiazepin- 5-one and methyl iodide. The yield was 71% of theory.

EXAMPLE 13

6,11-Dihydro-11-methyl-6-isopropyl-5H-pyrido[2,3-b][1,5]benzodiazepin-5-one

Using a procedure analogous to that described in Example 2, 6,11-dihydro-11-methyl-6 -isopropyl-5H-pyrido[2,3-b][1,5]benzodiazepin-5-one, m.p. 98°–100° C. (recrystallized from petroleum ether) was prepared from 6,11-dihydro-6-isopropyl-5H-pyrido[2,3-b][1,5]benzodiazepin- 5-one and methyl iodide. The yield was 61% of theory.

EXAMPLE 14

6-Butyl-6,11-dihydro-11-methyl-5H-pyrido-[2,3-b][1,5]benzodiazepin-5-one

Using a procedure analogous to that described in Example 2, the product 6-butyl-6,11 -dihydro-11-methyl-5H-pyrido[2,3-b][1,5]benzodiazepin-5-one, a colorless, viscous liquid of b.p. 150°–152° C. (0.03 mm Hg) was prepared from 6-butyl-6,11-dihydro-5H-pyrido[2,3 -b][1,5]benzodiazepin-5-one and methyl iodide. The yield was 57% of theory.

EXAMPLE 15

6,11-Dihydro-2,6,8,9,11-pentamethyl-5H-pyrido-[2,3-b][1,5]benzodiazepin-5-one

Using a procedure analogous to that described in Example 2, the product 6,11-dihydro-2,6,8,9,11-pentamethyl-5H-pyrido[2,3-b][1,5]benzodiazepin-5-one, m.p. 143–145! C (recrystallized from methanol) was prepared from 6,11-dihydro-2,6,8,9-tetramethyl-5H-pyrido[2,3-b][1,5]benzodiazepin-5-one and methyl iodide. The yield was 13% of theory.

EXAMPLE 16

6,11-Dihydro-2,4,6,8,9,11-hexamethyl-5H-pyrido-[2,3-b][1,5]benzodiazepin-5-one

Using a procedure analogous to that described in Example 2, the product 6,11-dihydro-2,4,6,8,9,11-hexamethyl-5H-pyrido[2,3-b][1,5]benzodiazepin-5-one, m.p. 148°–151° C. (recrystallized from ligroin, b.p. 100°–140° C.) was prepared from 6,11-Dihydro-2,4,6,8,9 -pentamethyl-5H-pyrido-[2,3-b][1,5]benzodiazepin-5-one and methyl iodide. The yield was 44% of theory.

EXAMPLE 17

Mixture of 6,11-Dihydro-2,4,6,8 11-and 6,11-dihydro-2,4,6,9,11-pentamethyl-5H-pyrido[2,3 -b][1,5]benzodiazepin-5-one Using a procedure analogous to that described in Example 2, a mixture of 6,11-dihydro-2,4,6,8 11- and 6,11-dihydro-2,4,6,9,11-pentamethyl-5H-pyrido[2,3-b][1,5]benzodiazepin-5one, m.p. 174°–176° C. (recrystallized from ligroin, b.p. 100°–140° C.) was prepared from a mixture of 6,11-dihydro-2,4,6,8 and 6,11-dihydro-2,4,6,9-tetramethyl-5H-pyrido[2,3 -b][1,5]benzodiazepin-5-one and methyl iodide. The yield was 12% of theory.

EXAMPLE 18

11-Acetyl-6,11-dihydro-6-methyl-5H-pyrido-[2,3-b][1,5]benzodiazepin-5-one 5.0 g (0.0222 mol) of 6,11-dihydro-6-methyl-5H-pyrido-[2,3-b][1,5]benzodiazepin-5-one were suspended in a mixture consisting of 2.0 g (0.0255 mol) of acetyl chloride, 10 ml benzene and 2.2 g (0.022 mol) of triethylamine and the resulting suspension was refluxed for 7 hours while stirred. The reaction mixture was filtered while hot, and the filtrate was evaporated in vacuo. The residue was twice recrystallized from cyclohexane using animal charcoal as an absorbent, yielding a colorless compound having a melting point of 140°–142° C., which was identified as 11-acetyl-6,11-dihydro-6-methyl-5H-pyrido[2,3-b][1,5]benzodiazepin-5-one. The yield was 59% of theory.

EXAMPLE 19

11-Acetyl-6,11-dihydro-6,8,9-trimethyl-5H-pyrido-[2,3-b][1,5]benzodiazepin-5-one Using a procedure analogous to that described in Example 18, the product 11-acetyl-6,11-dihydro-6,8,9-trimethyl-5H-pyrido[2,3-b][1,5]benzodiazepin-5-one, m.p. 168°–170° C. (recrystallized from cyclohexane) was prepared from 6,11-dihydro-6,8,9-trimethyl-5H-pyrido[2,3-b][1,5]benzodiazepin-5-one and acetyl chloride. The yield was 43% of theory.

EXAMPLE 20

6,11-bis-(methylthiomethyl)-9-chloro-6,11-dihydro-5H-pyrido[2,3-b][1,5]benzodiazepin-5-one Using a procedure analogous to that described in Example 2, the product 6,11-bis-(methylthiomethyl)-9-chloro-6,11-dihydro-5H-pyrido[2,3-b][1,5]benzodiazepin-5-one, m.p. 181°–182° C. (recrystallized from 1,2-dichloroethane) was prepared from 9-chloro-6,11-dihydro-5H-pyrido[2,3-b][1,5]benzodiazepin-5-one and 2 equivalents of methylthiomethyl chloride. The yield was 31% of theory.

EXAMPLE 21

6,11-Diethyl-5H-pyrido[2,3-b][1,5]benzodiazepin-5-one a) 5H-Pyrido[2,3-b][1,5]benzodiazepin-5-one 46 g of o-phenylenediamine (0.43 mol) and 46 g of 2-chloronicotinic acid (0.29 mol) were mixed and heated to between 110° and 120° C. The mixture melted and an exothermic reaction ensued. The reaction mixture was thereafter heated for two hours at 120° C., cooled and then washed with ethanol. The crude product was crystallized from acetic acid to yield 5H-pyrido[2,3-b][1,5]benzodiazepin-5-one as a yellow solid (449), m.p. 280°–285° C.

b) 6,11-Diethyl-5H-pyrido[2,3-b][1,5]benzodiazepin-5-one 5 g of the compound prepared above (0.024 mol) and 1.2 g of sodium hydride (0.05 mol) were heated in dry dimethylformamide (100 ml) for two hours. Ethyl iodide ((7.48 g; 0.048 mole) was then added dropwise over 10 minutes while maintaining the temperature at 35°–40° C. The reaction mixture was stirred overnight at room temperature and then poured into cold water. The resulting mixture was extracted with ether, the ether extract dried over anhydrous sodium sulfate, filtered and evaporated to dryness. The resulting oil was purified through silica gel chromatography, and crystallized from n-heptane to yield the title compound (2.3 g), m.p. 108°–110° C.

EXAMPLE 22

5,11-Dihydro-11-ethyl-6-methyl-5H-pyrido-[2,3-b][1,5]benzodiazepin-5-thione

A mixture of 4.00 (0.016 mol) of 6,11-dihydro-11-ethyl-6-methyl-5-pyrido[2,3-b][1,5]benzodiazepin-5-one, prepared as in Example 2, and 3.2 g (0.008 mol) of Lawesson's reagent [2,4-bis(4-methoxyphenyl)-1,3-dithia-2,4-diphosphetane-2,4-disulfide] in 50 ml of toluene was refluxed for 2½ hr. The solvent was then removed in vacuo and the residue purified on a silica gel column using methylene chloride. Removal of the solvent in vacuo gave 3.2 g (75%) of yellow oil. The oil was dissolved in cyclohexane and after standing at room temperature a yellow solid resulted. Recrystallization from cyclohexane gave 2.1 g (49% theory), of yellow needles, m.p. 103°–106° C., which was identified to be 5,11-dihydro-11-ethyl-6-methyl-5H-pyrido[3,2-b][1,5]diazepin-5-thione.

EXAMPLE 23

6,11-Dihydro-11-ethyl-5H-pyrido[2,3-b][1,5]-benzodiazepin-5-one

A mixture of 15 g of 6,11-dihydro-5H-pyrido[2,3-b][1,5]benzodiazepin-5-one and 150 ml DMF was heated to 50° C. To the slurry was added 7.5 g (2 equiv) of 50% sodium hydride in mineral oil dispersion, during which time the temperature rose to 65° C. The mixture was cooled to 40° C. and then 6.0 ml of iodoethane was added. The resulting mixture was stirred at room temperature overnight, then poured into 700 ml of water and extracted with 700 ml of ether. The ether phase was dried (MgSO$_4$) and concentrated to dryness. The crude product was purified by column chromatography on basic alumina to yield 3.6 g (21% of theory) of 6,11-dihydro-11-ethyl-5H-pyrido[2,3-b][1,5]benzodiazepin-5-one, m.p. 210°–220° C.

EXAMPLE 24

6,11-Dihydro-11-ethyl-5H-pyrido[2,3-b][1,5]-benzodiazepin-5-thione

To 2.2 g of 6,11-dihydro-11-ethyl-5-pyrido[2,3-b][1,5]benzodiazepin-5-one, prepared as in Example 23, was added 1.9 g of Lawesson's Reagent and 50 ml of toluene. The mixture was heated to reflux for 2½ hours and then cooled to room temperature. The reaction mixture was concentrated in vacuo and the solid residue was dissolved in methylene chloride. The resulting solid was filtered and recrystallized from ethyl acetate to yield 0.66 g (28% of theory) of 6,11-dihydro-11-ethyl-5H-pyrido[2,3-b][1,5]benzodiazepin-5-thione, m.p. 194°–196° C.

EXAMPLE 25

6,11-Dihydro-11-benzyl-6-methyl-5H-pyrido-[2,3-b][1,5]benzodiazepin-5-one

To a mixture of 4.0 g of 6,11-dihydro-6-methyl-5H-pyrido[2,3-b][1,5]benzodiazepin-5-one and 100 ml of dry DMF was added 1.2 g of 50% NaH in mineral oil. The resulting solution was heated to 60° C. for one hour. The dark red solution was cooled to 30° C. and 2.5 ml of benzyl bromide was added and stirred overnight under nitrogen. Methanol was added slowly until bubbling ceased, and the reaction mixture was then poured into 400 ml of water. The product was extracted with ether, dried over MgSO$_4$, then concentrated and purified by column chromatography over silica gel. Elution of the material with 2% ethyl acetate/methylene chloride gave a white solid, which was recrystallized from methylene chloride/ether/petroleum ether to give 2.2 g (39% of theory) of 6,11-dihydro-11-benzyl-6-methyl-5H-pyrido[2,3 -b][1,5]benzodiazapin-5-one, m.p. 168°–170° C.

EXAMPLE 26

5,6-Dihydro-11-(t-butoxycarbonyl)methyl-6-methyl-11H-pyrido[2,3-b ][1,5]benzodiazepin-5-one To 0.8 g (3.5 mmoles) of 5,6-dihydro-6-methyl-11H-pyrido[2,3-b][1,5]benzodiazepin-5-one in 75 ml of dimethylformamide was added 0.2 g (4.0 mmol) of 50% sodium hydride in oil, and the reaction mixture was stirred at 60° C. for 2 h. It was then cooled to room temperature and 0.78 g (4.0 mmoles) of t-butyl bromoacetate was added dropwise, and the reaction mixture was allowed to stir overnight. Excess sodium hydride was carefully quenched with water and the solvent was evaporated. The residue was dissolved in methylene chloride, washed with water and dried over anhydrous sodium sulfate. Evaporation of the solvent gave 2.0 g of crude product. Purification by column chromatography (silica gel) using 10% ethyl acetate/methylene chloride afforded 0.52 g of pure 5,6-Dihydro-11-(t-butoxycarbonyl)methyl-6 -methyl-11H-pyrido[2,3-b][1,5]benzodiazepin-5-one, m.p. 64°–65° C.

EXAMPLE 27

5,6-Dihydro-11-(ethoxycarbonyl)methyl-6-methyl-11H-pyrido[2,3-b][1,5]benzodiazepin-5-one To 1.0 g (4.4 mmoles) of 5,6-dihydro-6-methyl-11H-pyrido[2,3-b][1,5]benzodiazepin-5 -one in 50 ml of dimethylformamide was added 0.25 g (5 mmol) of 50% sodium hydride in oil. The reaction mixture was then stirred at 50° C. for an additional 2 h and then 0.6 ml (5 mmol) of ethyl bromoacetate was added. The reaction mixture was then stirred at 50° C. for an additional 3 h. It was then cooled to room temperature and the solvent was evaporated. The residue was dissolved in methylene chloride, washed with water, dried over anhydrous sodium sulfate and evaporated to obtain 2.0 g of the crude product. It was further purified by column chromatography (silica gel) using 10% ethyl acetate/methylene chloride as eluent to obtain 250 mg of pure 5,6-dihydro-11-(ethoxy-carbonyl)methyl-6-methyl-11H-pyrido[2,3 -b][1,5]benzodiazepin-5-one, m.p. 99°–100° C.

EXAMPLE 28

6,11-Dihydro-6,8,9-trimethyl-5H-pyrido-[2,3-b][1,5]benzodiazepin-5-one

To a stirred suspension of 4.55 g (0.019mol) of 6,11-dihydro-8,9-dimethyl-5H-pyrido[2,3 -b][1,5]benzodiazepin-5-one in 40 ml of dimethylsulfoxide was added 3.0 ml of a 30% NaOH solution (0.022 mol). After two hours at room temperature 5.0 ml (0.08 mol) of methyl iodide was added and the mixture stirred at room temperature overnight. It was then poured into water, the resulting precipitate collected, washed, dried and crystallized from ethanol to yield 3.3 g (69% of theory) of a crystallized solid melting at 206°–209° C.

EXAMPLE 29

6,11-Dihydro-11-ethyl-6,8,9-trimethyl-5H-pyrido-[2,3-b][1,5]benzodiazepin-5-one

Using a procedure analogous to that described in Example 2, the product 6,11-dihydro-11 -ethyl 6,8,9-trimethyl-5H-pyrido[2,3-b][1,5]benzodiazepin-5-one, m.p. 140°–144° C. (crystallized from petroleum ether) was prepared from 6,11-dihydro-6,8,9-trimethyl-5H-pyrido[2,3 -b][1,5]benzodiazepin-5-one, prepared as in Example 28, and ethyl iodide. The yield was 41% of the theory.

EXAMPLE 30

6,11-Dihydro-8-methoxycarbonyl-11-ethyl-6-methyl-5H-pyrido[2,3-b][1,5]benzodiazepin-5-one a) 6,11-Dihydro-8-methoxycarbonyl-5H-pyrido[2,3-b][1, 5]benzodiazepin-5-one A stirred mixture of 1.66 g (0.010 mol) of 4-methoxycarbonyl-o-phenylene-diamine and 1.58 g (0.010 mol) of 2-chloronicotinic acid in 5 ml of 2-butoxyethanol was heated to 140° C. for 2 h, during which time a dark solution, followed by formation of a green solid, was observed. The reaction mixture was poured into 50 ml of water and the solid collected and stirred in 10% sodium carbonate solution for 1 h. The resulting solid was collected, washed thoroughly with water, dried and crystallized from DMF to yield 1.1 g (40% of theory) of a beige crystalline product, m.p. 344°–349° C.

b) 6,11-Dihydro-8-methoxycarbonyl-6-methyl-5H-pyrido[2,3-b][1,5]benzodiazepin-5-one Using a procedure analogous to that described in Example 28, the product 6,11-dihydro-8 -methoxycarbonyl-6-methyl-5H-pyrido[2,3-b][1,5]benzodiazepin-5-one, m.p. 273°–276° C. (after trituration with ethanol) was prepared from 6,11-dihydro-8-methoxycarbonyl-5H-pyrido[2,3 -b][1,5]benzodiazepin-5-one and methyl iodide. The yield was 74% of theory.

c) 6,11-Dihydro-8-methoxycarbonyl-11-ethyl-6-methyl-5H-pyrido[2,3-b][1,5]benzodiazepin-5-one.

Using a procedure analogous to that described in Example 28, the product 6,11-dihydro-8 -methoxycarbonyl-11-ethyl-6-methyl-5H-pyrido[2,3-b][1,5]benzodiazepin-5-one, m.p. 137°–140° C. (crystallized from petroleum ether, (60°–90° C.) was prepared from 6,11-dihydro-8 -methoxycarbonyl-6-methyl-5H-pyrido[2,3-b][1,5]benzodiazepin-5-one and ethyl iodide. The yield was 32% of theory.

EXAMPLE 31

6,11-Dihydro-6-ethyl-7-methyl-5H-pyrido-[2,3-b][1,5]benzodiazepin-5-one

To a stirred suspension of 1.1 g (5 mmol) 6,11-dihydro-7-methyl-5H-pyrido-[2,3 -b][1,5]benzodiazepin-5-one in 20 ml of dry DMF 0.13 g (5.5 mmol) of sodium hydride was added portionwise at room temperature. Once the evolution of hydrogen had ceased, the mixture was heated to 60° C. for 2 h, cooled to 10° C., and then 0.86 g (5.5 mmol) of ethyl iodide was added. The reaction mixture was stirred at room temperature overnight and then concentrated. The residue was poured into water, the solid collected, washed, dried and column chromatographed on 60 g of dry silica gel. The product (second fraction) was eluted with methylene chloride and methylene chloride/methanol 99/1 to give 0.6 g (80% of theory) of 6,11-Dihydro-6-ethyl-7-methyl-5H-pyrido[2,3-b][1,5]benzodiazepin-5-one m.p. 186°–188° C.

EXAMPLE 32

6,11-Dihydro-7-methyl-5H-pyrido-[2,3-b][1,5]benzodiazepin-5-one

Using a procedure analogous to that described in Example 30, the product 6,11-dihydro-7-methyl-5H-pyrido[2,3-b][1,5]benzodiazepin-5-one, m.p. 233°–235° C. (crystallized from dioxane/water) was prepared from 3-methyl-o-phenylenediamine and 2-chloronicotinic acid. The yield was 35% of theory.

EXAMPLE 33

6,11-Dihydro-11-(2-fluoroethyl)-6-methyl-5H-pyrido-[2,3-6][1,5]benzodiazepin-5-one Using a procedure analagous to that described in Example 2, the product 6,11-dihydro-11-(2-fluoroethyl)-6-methyl-5H-pyrido[2,3-b][1,5]benzodiazepin-5-one, m.p. 118°–120° C., was obtained (87% of theory) from 6,11-dihydro-6-methyl-5H-pyrido[2,3-b][1,5]-benzodiazepin-5-one and 1-bromo-2-fluoroethane.

EXAMPLE 34

6,11-Dihydro-11-ethyl-6-fluoromethyl-5H-pyrido--[2,3-b][1,5]benzodiazepin-5-one a) 6,11-Dihydro-6-fluoromethyl-5H-pyrido[2,3-b][1,5]benzodiazepin-5-one Using a procedure analogous to that described in Example 2, the product 6,11-dihydro-6-fluoromethyl-5H-pyrido[2,3-b][1,5]benzodiazepin-5-one, m.p. 108°–110° C., was obtained (3% of theory) from 6,11-dihydro-5H-pyrido[2,3-b][1,5]benzodiazepin-5-one and bromofluoromethane.

b) 6-11-Dihydro-11-ethyl-6-fluoromethyl-5H-pyrido[2,3-b][1,5]benzodiazepin- 5-one Using a procedure analogous to that described in Example 2, the product 6,11-dihydro-11-ethyl-6-fluoromethyl-5H-pyrido[2,3-b][1,5]benzodiazepin-5-one, m.p. 113°–116° C., was obtained (69% of theory) from 6,11-dihydro-6-fluoromethyl-5H-pyrido[2,3-b][1,5]benzodiazepin- 5-one and ethyl iodide.

EXAMPLE 35

6,11-Dihydro-11-ethyl-6-methyl-9-nitro-5H-pyrido-[2,3-b][1,5]benzodiazepin-5-one a) A mixture of 2-chloronicotinic acid (15.7 g, 0.1 mol) and 4-nitrophenylene diamine (15.3 g, 0.1 mol) was heated in sulfonane (100 ml) at 170° C. for 5 hrs. The reaction mixture was then cooled and left standing overnight. The solid material was filtered and taken up in boiling ethanol. The solid was filtered again an dried giving 21 g (82% theory) of 6,11-dihydro-9-nitro-5H-pyrido[2,3-b][1,5]benzodiazepin-5-one suitable for use in the next reaction.

b) Sodium hydride (50% dispersion in oil, 4.0 g, 83 mmoles) was placed in a 3-neck round bottom flask. After washing the sodium hydride three times with hexane, DMSO (200 mL) was added. The mixture was heated to 50° C. until a clear solution was obtained and 21 g of the product obtained in step a) was added as a solution/suspension in DMSO (100 mL). The mixture was stirred for 1 hour at which time methyl iodide (12 g, 80 mmoles) was added, and the mixture was stirred at room temperature overnight. Water (200 ml) was added to the reaction mixture and the precipitate filtered. The solid material was treated twice with 300 ml portions of boiling ethanol for one hour and the combined filtrates were left standing at room temperature. Three crops of crystals were deposited over 4 days yielding 6.7 g (25% of theory) of 6,11-dihydro-6-methyl-9-nitro-5H-pyrido[2,3-b][1,5]benzodiazepin-5-one m.p. 275°–278° C.

c) To sodium hydride (50% in oil, 0.27 g, 5.6 mmoles) was added THF 1 ml. The mixture was swirled, the THF removed by pipette. DMSO (5 ml) was added and the mixture stirred and heated at 50° C. for 30 min. The product obtained the preceding step (1.5 g, 5.5 mmoles) was added as a solution/suspension in DMSO (5 ml) and stirred for 20 min. Ethyl iodide (0.98 g, 6.3 mmoles) was added and the mixture was stirred an additional 30 min. The reaction was quenched with water (100 ml) and extracted with methylene chloride. The organic phase was washed with water three times, dried (mgSO$_4$), filtered and concentrated in vacuo. Column chromatography over silica gel (Eluent methylene chloride ethanol:99/1) gave 0.5 g (30% of theory) of 6-11-dihydro-11-ethyl-6-methyl-9-nitro-5H-pyrido[2,3-b][1,5]benzodiazepin-5-one m.p. 179.5°–180.5° C., after recrystallization from ethanol/hexane.

EXAMPLE 36

6,11-Dihydro-9-amino-11-ethyl-6-methyl-5H-pyrido-[2,3b][1,5]benzodiazepin-5-one To a solution of 0.3 g (1 mmol) of 6,11-dihydro-11-ethyl-6-methyl-9-nitro-5H-pyrido[2,3 -b][1,5]benzodiazepin-5-one in acetic acid (5 ml) was added a solution of SnCl$_2$.2H$_2$O (1.7 g) in concentrated hydrochloric acid (2.2 ml). The mixture was stirred at room temperature for 6 hours, and then poured into a saturated sodium bicarbonate solution and made basic with aqueous sodium hydroxide. The aqueous phase was then extracted with ethyl acetate, dried (MgSO$_4$), filtered and concentrated in vacuo. The solid material obtained was recrystallized from ethyl acetate to give 0.12 g (44% of theory) of 6,11-dihydro-9-amino-11-ethyl-6-methyl-5H-pyrido[2,3-b][1,5]benzodiazepin-5-one, m.p. 193°–195° C.

EXAMPLE A

| | Capsules or Tablets | | |
| --- | --- | --- | --- |
| A-1 | | A-2 | |
| Ingredients | Quantity | Ingredients | Quantity |
| Compound of Ex. 2 | 250 mg | Compound of Ex. 2 | 50 mg |
| Starch | 160 mg | Dicalcium Phosphate | 160 mg |
| Microcrys. Cellulose | 90 mg | | |
| Sodium Starch Glycolate | 10 mg | Microcrys. Cellulose | 90 mg |
| Magnesium Stearate | 2 mg | Stearic acid | 5 mg |
| Fumed colloidal silica | 1 mg | Sodium Starch Glycolate | 10 mg |
| | | Fumed colloidal silica | 1 mg |

The compound of Example 2 is blended into a powder mixture with the premixed excipient materials as identified above with the exception of the lubricant. The lubricant is then blended in and the resulting blend compressed into tablets or filled into hard gelatin capsules.

EXAMPLE B

| Parenteral Solutions | |
|---|---|
| Ingredients | Quantity |
| Compound of Example 2 | 500 mg |
| Tartaric acid | 1.5 g |
| Benzyl Alcohol | 0.1% by weight |
| Water for injection | q.s. to 100 ml |

The excipient materials are mixed with the water and thereafter the compound of Example 2 is added. Mixing is continued until the solution is clear. The pH of this solution is adjusted to 3.0 and is then filtered into the appropriate vials or ampoules and sterilized by autoclaving.

EXAMPLE C

| Nasal Solutions | |
|---|---|
| Ingredients | Quantity |
| Compound of Example 2 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 ml |

The excipient materials are mixed with the water and thereafter the compound of Example 2 is added and mixing is continued until the solution is clear. The pH of this solution is adjusted to 4.0 and is then filtered into the appropriate vials or ampoules.

We claim:

1. A compound of the formula I

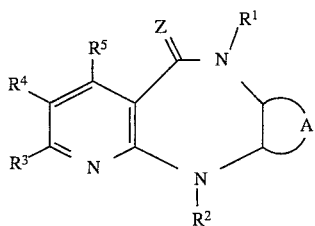

wherein,

A is a fused ring of the formula

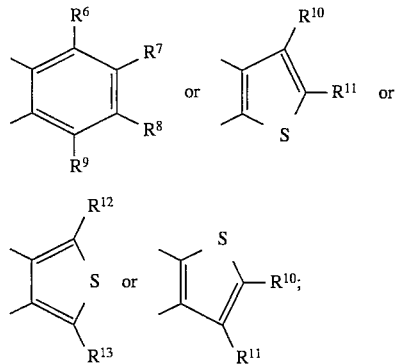

Z is oxygen, sulfur, =NCN, or a group of the formula =NOR$^{14}$ wherein R$^{14}$ is alkyl of 1 to 3 carbon atoms;

R$^1$ is hydrogen, alkyl or fluoroalkyl of 1 to 5 carbon atoms, cyclopropyl, alkenyl or alkynyl of 3 to 5 carbon atoms, 2-halo-propen-1-yl, arylmethyl (wherein the aryl moiety is phenyl, thienyl or furanyl, which is either unsubstituted or substituted by methyl, methoxy or halogen), alkanoyl of 2 to 3 carbon atoms, cyanoalkyl wherein the alkyl moiety contains 1 to 3 carbon atoms, or alkoxyallyl or alkylthioalkyl of 2 to 4 carbon atoms;

R$^2$ is alkyl or fluoroalkyl of 1 to 5 carbon atoms, cycloalkyl of 3 to 5 carbon atoms, alkenyl or alkynyl of 2 to 5 carbon atoms, alkoxyalkyl or alkylthioalkyl of 2 to 4 carbon atoms, alkanoyl of 2 to 4 carbon atoms, hydroxyalkyl of 2 to 5 carbon atoms, arylmethyl (wherein the aryl moiety is phenyl, thienyl or furanyl, which is either unsubstituted or substituted by alkyl or alkoxy of 1 to 3 carbon atoms, hydroxyl, or halogen), phenyl (which is either unsubstituted or substituted by alkyl or alkoxy of 1 to 3 carbon atoms, halogen or hydroxyl) or alkoxy-carbonylmethyl wherein the alkoxy moiety contains 1 to 5 carbon atoms;

R$^3$, R$^4$, and R$^5$ are each independently hydrogen, alkyl of 1 to 3 carbon atoms or chloro, with the proviso that at least one of these substituents is hydrogen; or, one of R$^3$, R$^4$ and R$^5$ is butyl, alkanoyl of 1 to 3 carbon atoms, hydroxyalkyl of 1 to 4 carbon atoms, alkoxycarbonyl of 2 to 3 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkythio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- or di-alkylaminocarbonyl wherein each alkyl moiety contains 1 to 2 carbon atoms, carboxyalkyl of 2 to 3 carbon atoms, cyano, nitro, carboxyl, carbamyl, amino, azido or mono- or di-alkylaminoalkyl wherein the alkyl moieties each contain 1 to 2 carbon atoms, and the remaining two substituents are hydrogen or methyl; or, when Z is oxygen, one of R$^3$, R$^4$ and R$^5$ is alkylsulfinyl or alkylsulfonyl of 1 to 3 carbon atoms, with the proviso that the remaining two substituents are hydrogrogen or methyl;

R$^6$, R$^7$, R$^8$ and R$^9$ are each hydrogen; or, one of R$^6$, R$^7$, R$^8$ and R$^9$ is alkyl of 1 to 4 carbon atoms, alkanoyl of 1 to 3 carbon atoms, alkoxycarbonyl of 2 to 3 carbon atoms, hydroxyalkyl of 1 to 4 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- or di-alkylaminocarbonyl wherein each alkyl moiety contains 1 to 2 carbon atoms, carboxylalkyl of 2 to 3 carbon atoms, cyano, nitro, carboxyl, carbamyl, amino, azido or mono- or di-alkylaminoalkyl wherein each alkyl moiety contains 1 to 2 carbon atoms, and the remaining three substituents are hydrogen or two of the remaining three substituents are hydrogen and one is methyl, ethyl or halogen;

R$^{10}$ or R$^{11}$ is hydrogen, alkyl of 1 to 4 carbon atoms, cyano, nitro, halogen or alkanoyl of 1 to 3 carbon atoms, with the remaining substituent being hydrogen, chloro, methyl or ethyl; and, R$^{12}$ and R$^{13}$ are each independently hydrogen, alkyl of 1 to 4 carbon atoms, halogen or nitro;

or a pharmaceutically acceptable acid addition salt thereof.

2. A compound of the formula Ia

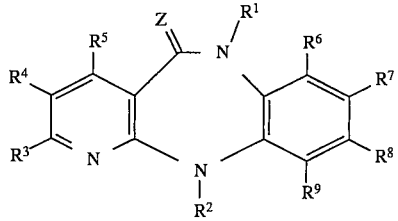

wherein,

Z is oxygen or sulfur;

$R^1$ is hydrogen, alkyl of 1 to 4 carbon atoms, alkenyl or alkynyl of 2 to 4 carbon atoms, 2-halo-propen-1-yl, or alkoxyalkyl or alkylthioalkyl of 2 to 3 carbon atoms;

$R^2$ is alkyl of 1 to 4 carbon atoms, cycloalkyl of 3 to 4 carbon atoms, alkenylmethyl or alkynylmethyl of 2 to 4 carbon atoms, alkoxyalkyl or alkylthioalkyl of 2 to 4 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy, hydroxyl or halogen), phenyl (which is either unsubstituted or substituted by methyl, methoxy, hydroxyl or halogen) or alkoxycarbonylmethyl wherein the alkoxy moiety contains 1 to 5 carbon atoms;

$R^3$, $R^4$, and $R^5$ are each independently hydrogen or methyl, with the proviso that at least one of these substituents is hydrogen, or $R^5$ is ethyl, propyl or butyl with the other two substituents being hydrogen;

$R^6$ is hydrogen, methyl, ethyl, chloro or trifluoromethyl with the proviso that $R^7$ is hydrogen, methyl or chloro;

$R^7$ is hydrogen, alkyl of 1 to 3 carbon atoms, alkanoyl of 1 to 3 carbon atoms, alkoxycarbonyl of 1 to 3 carbon atoms, hydroxyalkyl of 1 to 3 carbon atoms, alkoxycarbonylalkyl wherein the alkoxy and alkyl moieties each contain 1 to 2 carbon atoms, halogen, trifluoromethyl, hydroxyl, alkoxy or alkylthio of 1 to 2 carbon atoms, acetyloxy, alkanoylamino or aminoalkyl of 1 to 2 carbon atoms, cyano, nitro, amino, or mono- or di-methyl or -ethylamino, with the proviso that $R^8$ is hydrogen, methyl or chloro;

$R^8$ is hydrogen, alkyl of 1 to 3 carbon atoms, alkanoyl of 1 to 3 carbon atoms, alkoxycarbonyl of 1 to 3 carbon atoms, hydroxyalkyl of 1 to 3 carbon atoms, alkoxycarbonylalkyl wherein the alkoxy and alkyl moieties each contain 1 to 3 carbon atoms, halogen, trifluoromethyl, hydroxyl, alkoxy or alkylthio of 1 to 2 carbon atoms, acetyloxy, alkanoylamino or aminoalkyl of 1 to 2 carbon atoms, cyano, nitro, amino, or mono- or di-methyl or -ethylamino with the proviso that $R^7$ is hydrogen, methyl or chloro; or, when Z is oxygen and $R^8$ is hydrogen or methyl, $R^7$ may additionally be alkylsulfinyl or alkylsulfonyl of 1 to 2 carbon atoms, and when Z is oxygen and $R^7$ is hydrogen or methyl, $R^8$ may additionally be alkylsulfinyl or alkylsulfonyl of 1 to 2 carbon atoms; and, $R^9$ is hydrogen, methyl, ethyl, chloro or trifluoromethyl with the proviso that $R^8$ is hydrogen, methyl or chloro;

or a pharmaceutically acceptable acid addition salt thereof.

3. A compound of formula Ia, as set forth in claim 2, wherein,

Z is oxygen or sulfur;

$R^1$ is hydrogen, alkyl of 1 to 3 carbon atoms, 2-halo-2-propen-1-yl, or alkoxyalkyl or alkylthio-alkyl of two to three carbon atoms;

$R^2$ is alkyl of 1 to 4 carbon atoms, cycloalkyl of 3 to 4 carbon atoms, alkenyl or alkynyl of 2 to 4 carbon atoms, alkyloxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy or halogen) or alkoxycarbonylmethyl wherein the alkoxy moiety contains 1 to 5 carbon atoms; and, $R^3$ through $R^9$ are as set forth below in Table A:

TABLE A

| | $R^3$ | $R^4$ | $R^5$ | $R^6$ | $R^7$ | $R^8$ | $R^9$ |
|---|---|---|---|---|---|---|---|
| a | H | H | H | H | H | $CF_3$ | H |
| b | H | H | H | H | Cl | H | H |
| c | H | H | H | H | $CH_3$ | $CH_3$ | H |
| d | $CH_3$ | H | H | H | $CH_3$ | $CH_3$ | H |
| e | $CH_3$ | $CH_3$ | H | H | $CH_3$ | $CH_3$ | H |
| f | H | H | H | $CH_3$ | $CH_3$ | H | H |
| g | H | H | H | H | H | Cl | H |
| h | H | H | H | H | H | H | H |
| i | H | H | H | $CH_3$ | H | H | H |
| j | H | H | H | H | $CH_3O_2C-$ | H | H |
| k | H | H | H | H | $C_2H_5O_2C-$ | H | H |
| l | H | H | H | H | NC— | H | H |
| m | H | H | H | H | $CH_3CO-$ | H | H |
| n | H | H | H | H | H | $CH_3O_2C-$ | H |
| o | H | H | H | H | H | $C_2H_5O_2C-$ | H |
| p | H | H | H | H | H | NC— | H |
| q | H | H | H | H | H | $CH_3CO-$ | H |
| r | H | H | H | H | Cl | Cl | H |
| s | H | H | H | $CH_3$ | H | $CH_3$ | H |

4. A compound of formula Ia, as set forth in claim 2, wherein,

Z is oxygen or sulfur;

$R^1$ is hydrogen, alkyl of 1 to 2 carbon atoms or allyl;

$R^2$ is alkyl of 2 to 3 carbon atoms, cyclopropyl or allyl; and $R^3$ through $R^9$ are each hydrogen, or $R^7$ and $R^8$ are both methyl or chloro and $R^3$, $R^4$, $R^5$, $R^6$ and $R^9$ are each hydrogen.

5. A compound of formula Ia, in accordance with claim 2, selected from the group consisting of the following:

a) 6,11-dihydro-11-ethyl-6-methyl-5H-pyrido[2,3-b][1,5]benzodiazepin-5-one;

b) 6,11-dihydro-6-methyl-11-propyl-5H-pyrido[2,3-b][1,5]benzodiazepin-5-one;

c) 6,11-dihydro-6-methyl-11-methylethyl-5H-pyrido[2,3-b][1,5]benzodiazepin-5-one;

d) 6,11-dihydro-11-ethyl-5H-pyrido[2,3-b][1,5]benzodiazepin-5-one;

e) 6,11-dihydro-11-ethyl-5H-pyrido[2,3-b][1,5]benzodiazepin-5-thione;

f) 5,6-dihydro-6,8,9,11-tetramethyl-5H-pyrido[2,3-b][1,5]benzodiazepin-5-one;

g) 5,6-dihydro-6-ethyl-11-methyl-5H-pyrido[2,3-b][1,5]benzodiazepin-5-one;

h) 5,6-dihydro-6-n-propyl-11-methyl-5H-pyrido[2,3-b][1,5]benzodiazepin-5-one;

i) 5,6-dihydro-6-i-propyl-11-methyl-5H-pyrido[2,3-b][1,5]benzodiazepin-5-one;

j) 5,6-dihydro-6,11-diethyl-5H-pyrido[2,3-b][1,5]benzodiazepin-5-one;

k) 5,6-dihydro-11-ethyl-5H-pyrido[2,3-b][1,5]benzodiazepin-5-thione;

l) 5,6-dihydro-11-ethyl-6,8,9-trimethyl-5H-pyrido[2,3-b][1,5]benzodiazepin-5-one m) 5,6-dihydro-8-methoxycarbonyl-11-ethyl-6-methyl-5H-pyrido-[2,3-b][1,5]benzodiazepin-5-one; and, n) 5,6-dihydro-11-fluoroethyl-6-methyl-5H-pyrido[2,3-b][1,5]benzodiazepin-5-one.

6. 6,11-dihydro-11-ethyl-6-methyl-5H-pyrido[2,3-b][1,5]benzodiazepin-5-one.

7. 6,11-dihydro-11-ethyl-7-methyl-5H-pyrido[2,3-b][1,5]benzodiazepin-5-one.

8. A method for treating infection by HIV-1 which comprises administering to a human exposed to or infected by HIV-1 a therapeutically effective amount of a compound according to claims 1, 2, 3, 4, 5, 6 or 7.

9. A pharmaceutical composition suitable for the treatment of HIV-1 infection comprising a therapeutically effective mount of a compound according to claims 1, 2, 3, 4, 5, 6 or 7 and a pharmaceutically acceptable carrier.

10. A method for treating infection by HIV-1 which comprises administering to a human exposed to or infected by HIV-1 a therapeutically effective amount of a compound selected from the group consisting of:

a) 2,4,6,8 tetramethyl-6-11-dihydro-5H-pyrido[2,3-b][1,5]benzo-diazepin-5-one or -thione;

b) 6-methyl-6,11-dihydro-5H-pyrido[2,3-b][1,5]benzodiazepin-5-one or -thione;

c) 6-11-dihydro-5H-pyrido[2,3-b][1,5]benzodiazepin-5-one or -thione;

d) 6-ethyl-6,11-dihydro-5H-pyrido[2,3-b][1,5]benzodiazepin-5-one or -thione;

e) 6,8,9-trimethyl-6,11-dihydro-5H-pyrido[2,3-b][1,5]benzodiazepin-5-one or -thione;

e) 6,8,9-trimethyl-6,11-dihydro-5H-pyrido[2,3-b][1,5]benzodiazepin-5-one or -thione;

f) 6-ethyl-8,9-dimethyl-6,11-dihydro-5H-pyrido[2,3-b][1,5]benzo-diazepin-5-one or -thione;

g) 6-isobutyl-6,11-dihydro-5H-pyrido[2,3-b][1,5]benzodiazepin-5-one or -thione; and h) 6-ethyl-9-methyl-6,11-dihydro-5H-pyrido[2,3-b][1,5]benzodiazepin-5-one or -thione.

11. A pharmaceutical composition suitable for the treatment of HIV-1 infection comprising a therapeutically effective amount of a compound selected from the group consisting of:

a) 2,4,6,8 tetramethyl-6,11-dihydro-5H-pyrido[2,3-b][1,5]benzodiazepin-5-one or-thione;

b) 6-methyl-6,11-dihydro-5H-pyrido[2,3-b][1,5]benzodiazepin-5-one or -thione;

c) 6,11-dihydro-5H-pyrido[2,3-b][1,5]benzodiazepin-5-one or -thione;

d) 6-ethyl-6,11-dihydro-5H-pyrido[2,3-b][1,5]benzodiazepin-5-one or -thione;

e) 6,8,9-trimethyl-6,11-dihydro-5H-pyrido[2,3-b][1,5]benzodiazepin-5-one or -thione;

f) 6-ethyl-8,9-dimethyl-6,11-dihydro-5H-pyrido[2,3-b][1,5]benzo-diazepin-5-one or thione;

g) 6-isobutyl-6,11-dihydro-5H-pyrido[2,3-b][1,5]benzodiazepin-5-one or -thione; and h) 6-ethyl-9-methyl-6,11-dihydro-5H-pyrido[2,3-b][1,5]benzodiazepin-5-one or -thione;

and a pharmaceutically acceptable carrier.

12. A compound selected from the group consisting of the following:

a) 2,4,6,8 tetramethyl-6,11-dihydro-5H-pyrido[2,3-b][1,5]benzodiazepin-5-thione;

b) 6-methyl-6,11-dihydro-5H-pyrido[2,3-b][1,5]benzodiazepin-5-thione;

c) 6,11-dihydro-5H-pyrido[2,3-b][1,5]benzodiazepin-5-thione;

d) 6-ethyl-6,11-dihydro-5H-pyrido[2,3-b][1,5]benzodiazepin-5-thione;

e) 6,8,9-trimethyl-6,11-dihydro-5H-pyrido[2,3-b][1,5]benzodiazepin-5-thione;

f) 6-ethyl-8,9-dimethyl-6,11-dihydro-5H-pyrido[2,3-b][1,5]benzo-diazepin-5-thione;

g) 6-isobutyl-6,11-dihydro-5H-pyrido[2,3-b][1,5]benzodiazepin-5-thione; and h) 6-ethyl-9-methyl-6,11-dihydro-5H-pyrido[2,3-b][1,5]benzodiazepin-5-thione.

\* \* \* \* \*